US008740803B2

(12) United States Patent
Hersh et al.

(10) Patent No.: US 8,740,803 B2
(45) Date of Patent: Jun. 3, 2014

(54) USE OF THE FREQUENCY SPECTRUM OF ARTIFACT IN OSCILLOMETRY

(75) Inventors: Lawrence T. Hersh, Milwaukee, WI (US); Sai Kolluri, Tampa, FL (US)

(73) Assignee: General Electric Company, Schenectady, NY (US)

( * ) Notice: Subject to any disclaimer, the term of this patent is extended or adjusted under 35 U.S.C. 154(b) by 812 days.

(21) Appl. No.: 12/729,883

(22) Filed: Mar. 23, 2010

(65) Prior Publication Data

US 2011/0237962 A1 Sep. 29, 2011

(51) Int. Cl.
*A61B 5/02* (2006.01)

(52) U.S. Cl.
USPC ........... 600/493; 600/490; 600/494; 600/495; 600/500

(58) Field of Classification Search
USPC .................................. 600/490, 492–496, 485
See application file for complete search history.

(56) References Cited

U.S. PATENT DOCUMENTS

| | | | | |
|---|---|---|---|---|
| 5,913,826 | A * | 6/1999 | Blank | 600/500 |
| 7,678,059 | B2 | 3/2010 | Friedman et al. | |
| 2004/0138540 | A1 * | 7/2004 | Baker et al. | 600/336 |
| 2004/0267148 | A1 * | 12/2004 | Arand et al. | 600/528 |
| 2005/0143634 | A1 * | 6/2005 | Baker et al. | 600/310 |
| 2007/0118036 | A1 * | 5/2007 | Hersh et al. | 600/485 |
| 2009/0209868 | A1 | 8/2009 | Hersh et al. | |
| 2009/0326392 | A1 | 12/2009 | Kolluri et al. | |
| 2011/0112442 | A1 * | 5/2011 | Meger et al. | 600/595 |

FOREIGN PATENT DOCUMENTS

| | | | |
|---|---|---|---|
| CN | 1242693 | A | 1/2000 |
| CN | 101002672 | A | 7/2007 |

OTHER PUBLICATIONS

Unofficial translation of Chinese Official Action from CN Application No. 201010625183.8 dated Feb. 8, 2014.
Unofficial translation of Chinese Search Report from CN Application No. 201010625183.8 dated Feb. 8, 2014.

* cited by examiner

*Primary Examiner* — Michael Kahelin
*Assistant Examiner* — Tho Tran
(74) *Attorney, Agent, or Firm* — Andrus Intellectual Property Law, LLP

(57) ABSTRACT

A system and method for processing oscillometric data from a plurality of pressure steps to determine the blood pressure of a patient. A heart rate monitor connected to the patient acquires the patient's heart rate. A time-to-frequency domain converter receives oscillometric data and converts the oscillometric data into the frequency domain. Based upon the calculated heart rate, the system and method filters the frequency domain oscillometric signal with pass bands centered at the fundamental frequency and at least one fundamental frequency. The energy of the frequency domain signal within the pass bands is compared to at least a portion of the energy of the frequency domain oscillometric signal outside of the pass bands. Based upon the comparison, the signal determines whether the signal at the current pressure step should be utilized in calculating the blood pressure of the patient.

13 Claims, 8 Drawing Sheets

HEART RATE MONITOR 32
HEART RATE 58
PRESSURE TRANSDUCER 26
52
TIME TO FREQUENCY CONVERTER 54
56
64 FUNDAMENTAL FREQ. FILTER
76 1ST SET OF ARTIFACT FILTERS
66 FIRST HARMONIC FILTER
82 2ND SET OF ARTIFACT FILTERS
68 NTH HARMONIC FILTER
88 NTH SET OF ARTIFACT FILTERS
PASSBAND ENERGY ACCUMULATOR 94
ARTIFACT BAND ACCUMULATOR 96
98 RATIO CALCULATOR
100 WAVEFORM RECONSTRUCTOR

USE OF THE FREQUENCY SPECTRUM OF ARTIFACT IN OSCILLOMETRY

BACKGROUND OF THE INVENTION

The present disclosure generally relates to the field of non-invasive blood pressure monitoring. More specifically, the present disclosure relates to a method and system for filtering signals from a patient for the improved processing of artifact contaminated oscillometric data.

The human heart periodically contracts to force blood through the arteries. As a result of this pumping action, pressure pulses or oscillations exist in these arteries and cause them to cyclically change volume. The minimum pressure during each cycle is known as the diastolic pressure and the maximum pressure during each cycle is known as the systolic pressure. A further pressure value, known as the "mean arterial pressure" (MAP) represents a time-weighted average of the measured blood pressure over each cycle.

While many techniques are available for the determination of the diastolic, systolic, and mean arterial pressures of a patient, one such method typically used in non-invasive blood pressure monitoring is referred to as the oscillometric technique. This method of measuring blood pressure involves applying an inflatable cuff around an extremity of a patient's body, such as the patient's upper arm. The cuff is then inflated to a pressure above the patient's systolic pressure and then incrementally reduced in a series of small steps. A pressure sensor pneumatically connected to the cuff measures the cuff pressure throughout the deflation process. The sensitivity of the sensor is such that it is capable of measuring the pressure fluctuations occurring within the cuff due to blood flowing through the patient's arteries. With each beat, blood flow causes small changes in the artery volume which are transferred to the inflated cuff, further causing slight pressure variations within the cuff which are then detected by the pressure sensor. The pressure sensor produces an electrical signal representing the cuff pressure level combined with a series of small periodic pressure variations associated with the beats of a patient's heart for each pressure step during the deflation process. It has been found that these variations, called "complexes" or "oscillations," have a peak-to-peak amplitude which is minimal for applied cuff pressures above the systolic pressure.

As the cuff pressure is decreased, the oscillation size begins to monotonically grow and eventually reaches a maximum amplitude. After the oscillation size reaches the maximum amplitude, the oscillation size decreases monotonically as the cuff pressure continues to decrease. Oscillometric data such as this is often described as having a "bell curve" appearance. Indeed, a best-fit curve, or envelope, may be calculated representing the measured oscillometric pulses. Physiologically, the cuff pressure at the maximum oscillation amplitude value approximates the MAP. In addition, complex amplitudes at cuff pressures equivalent to the systolic and diastolic pressures have a fixed relationship to this maximum oscillation amplitude value. Thus, the oscillometric method is based upon measurements of detected oscillation amplitudes at various cuff pressures.

Blood pressure measuring devices operating according to the oscillometric method detect the amplitude of the pressure oscillations at various applied cuff pressure levels. The amplitudes of these oscillations, as well as the applied cuff pressure, are stored together as the device automatically changes the cuff pressures through a predetermined pressure pattern. These oscillation amplitudes define an oscillometric "envelope" and are evaluated to find the maximum value and its related cuff pressure, which is approximately equal to MAP. The cuff pressure below the MAP value which produces an oscillation amplitude having a certain fixed relationship to the maximum value is designated as the diastolic pressure, and, likewise, the cuff pressures above the MAP value which results in complexes having an amplitude with a certain fixed relationship to that maximum value is designated as the systolic pressure. The relationships of oscillation amplitude at systolic and diastolic pressures, respectively, to the maximum value at MAP are empirically derived ratios depending on the preferences of those of ordinary skill in the art. Generally, these ratios are designated in the range of 40%-80% of the amplitude at MAP.

One way to determine oscillation magnitudes is to computationally fit a curve to the recorded oscillation amplitudes and corresponding cuff pressure levels. The fitted curve may then be used to compute an approximation of the MAP, systolic, and diastolic data points. An estimate of MAP is taken as the cuff pressure level with the maximum oscillation. One possible estimate of MAP may therefore be determined by finding the point on the fitted curve where the first derivative equals zero. From this maximum oscillation value data point, the amplitudes of the oscillations at the systolic and diastolic pressures may be computed by taking a percentage of the oscillation amplitude at MAP. In this manner, the systolic data point and the diastolic data point along the fitted curve may each be computed and therefore their respective pressures may also be estimated. This curve fitting technique has the advantage of filtering or smoothing the raw oscillometric data. However, in some circumstances it is been found that additional filtering techniques used to build and process the oscillometric envelope could improve the accuracy of the determination of the blood pressure values.

The reliability and repeatability of blood pressure computations hinges on the ability to accurately determine the oscillation amplitude. However, the determination of the oscillation amplitudes is susceptible to artifact contamination. As the oscillometric method is dependent upon detecting tiny fluctuations in measured cuff pressure, outside forces affecting this cuff pressure may produce artifacts that in some cases may completely mask or otherwise render the oscillometric data useless. One such source of artifacts is from voluntary or involuntary motion by the patient. Involuntary movements such as the patient shivering may produce high frequency artifacts in the oscillometric data. Voluntary motion artifacts, such as those caused by the patient moving his or her arm, hand, or torso, may produce low frequency artifacts.

Presently available systems may be able to determine whether or not collected oscillometric data has been corrupted with artifact; however, current filtering techniques are ineffective at removing artifacts that have similar frequency content as the desired oscillometric data. Alternatively, non-invasive blood pressure systems may simply reject oscillometric data that has been designated as being corrupted by artifacts. In these instances, more oscillometric data must be collected at each pressure step until reasonably artifact free oscillometric data may be acquired. This may greatly lengthen the time for determination of a patient's blood pressure and submit the patient to increased discomfort that is associated with the inflatable cuff restricting blood flow to the associated extremity.

SUMMARY OF THE INVENTION

A method of computing an oscillometric envelope for use in determining the blood pressure of a patient is disclosed herein. The method includes the steps of receiving an oscillometric signal and an indication of a patient's heart rate. Next, the fundamental frequency and at least one harmonic frequency of the heart rate are found using a different physiological parameter such as the SpO2 or ECG. The oscillometric data is then converted to the frequency domain.

Once the oscillometric data has been converted to the frequency domain, the frequency domain oscillometric signal is filtered using one or more band pass filters having a pass band centered around the fundamental frequency and one or more harmonic frequencies. The energy within the pass bands centered around the fundamental frequency and the one or more harmonic frequencies are determined. Additionally, the method and system calculates the energy of the frequency domain oscillometric signal in at least a portion of the signal outside of the one or more pass bands. In one embodiment, the energy of the frequency domain oscillometric signal can be calculated in artifact bands positioned slightly above and slightly below the pass bands.

Once the energy within the pass bands and the energy outside of the pass bands has been calculated, the method and system calculates a ratio of the energy within the pass bands to the energy outside of the pass bands. If the calculated ratio exceeds a threshold, the system proceeds to calculate the oscillometric signal from the filtered frequency domain signal in the pass bands and computes an oscillometric envelope data point.

If the ratio does not exceed a threshold, the system can obtain additional oscillometric data at the current pressure step before moving to the next pressure step. Alternatively, the system can determine which of the pass bands to use in reconstructing the oscillometric signal. Finally, the comparison of the energy within the pass bands to the energy outside of the pass bands can be utilized by the system and method to determine a quality value of the blood pressure reading.

BRIEF DESCRIPTION OF THE DRAWINGS

The drawings illustrate the best mode presently contemplated of carrying out the disclosure. In the drawings.

DETAILED DESCRIPTION OF THE INVENTION

Figure 1:
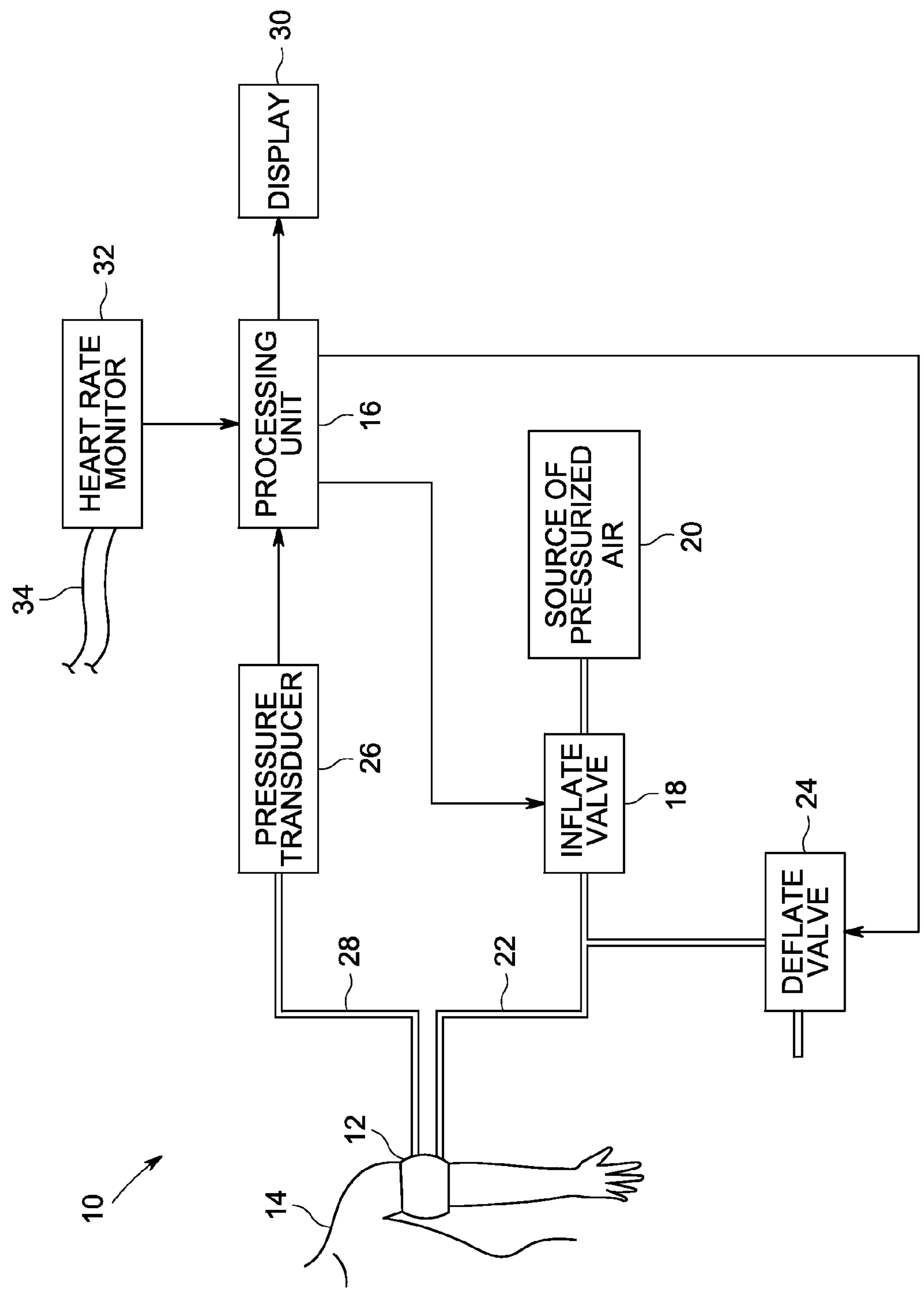
FIG. 1 depicts an embodiment of a system for the non-invasive measurement of blood pressure.

FIG. 1 depicts an embodiment of a non-invasive blood pressure (NIBP) monitoring system 10. The NIBP monitoring system 10 includes a pressure cuff 12 that is a conventional flexible, inflatable and deflatable cuff worn on the arm or other extremity of a patient 14. A processing unit 16 controls an inflate valve 18 that is disposed between a source of pressurized air 20 and a pressure conduit 22. As the inflate valve 18 is controlled to increase the pressure in the cuff 12, the cuff 12 constricts around the arm of the patient 14. Upon reaching a sufficient amount of pressure within the cuff 12, the cuff 12 fully occludes the brachial artery of the patient 14.

After the cuff 12 has been fully inflated, the processing unit 16 further controls a deflate valve 24 to begin incrementally releasing pressure from the cuff 12 back through pressure conduit 22 and out to the ambient air. During the inflation and incremental deflation of the cuff 12, a pressure transducer 26, pneumatically connected to the pressure cuff 12 by pressure conduit 28 measures the pressure within the pressure cuff 12. In an alternative embodiment, the cuff 12 is continuously deflated as opposed to incrementally deflated. In such continuously deflating embodiments, the pressure transducer 26 may measure the pressure within the cuff continuously or incrementally at regular intervals.

As the pressure within the cuff 12 decreases, the pressure transducer 26 will detect oscillometric pulses in the measured cuff pressure that are representative of the pressure fluctuations caused by the patient's blood flowing into the brachial artery with each heart beat and the resulting expansion of the artery to accommodate the additional volume of blood.

The cuff pressure data as measured by the pressure transducer 26, including the oscillometric pulses, is provided to the processing unit 16 such that the cuff pressure data may be processed and analyzed and a determination of the patient's blood pressure, including systolic pressure, diastolic pressure and MAP can be displayed to a clinician on a display 30.

The processing unit 16 may further receive an indication of the heart rate of the patient 14 as acquired by a heart rate monitor 32. The heart rate monitor 32 acquires the heart rate of the patient 14 using one or more of a variety of commonly used heart rate detection techniques. One heart rate detection technique that may be used would be that of electrocardiography (ECG) wherein electrical leads 34 connected to specific anatomical locations on the patient 14 monitor the propagation of the electrical activity through the patient's heart. Alternatively, the patient's heart rate may be acquired using $Sp0_2$, plethysmography, or other known techniques, including signal processing and analysis of the cuff pressure data.

Figure 2:
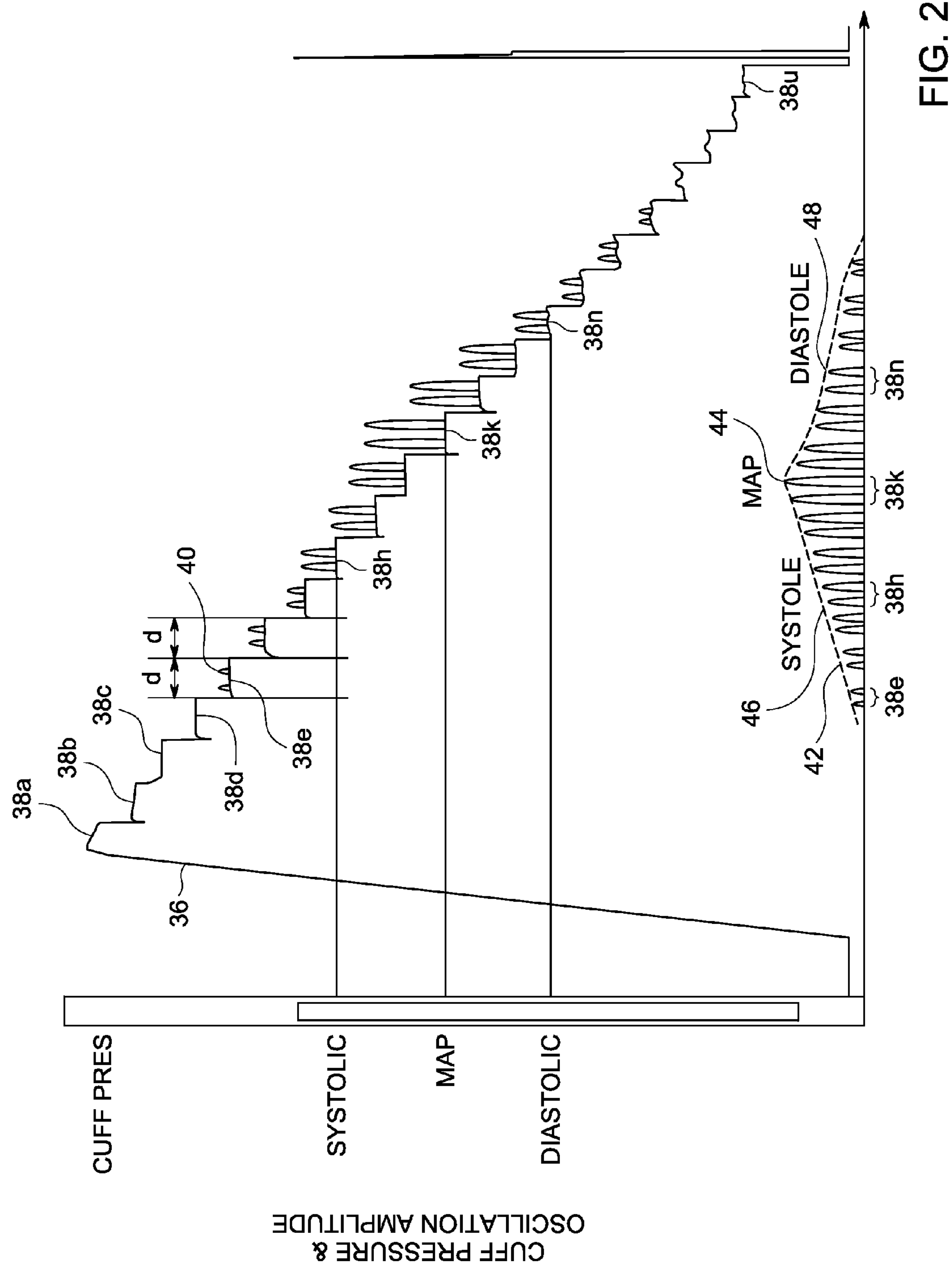
FIG. 2 is a graph depicting the oscillometric data collected from a blood pressure cuff at multiple pressure steps.

FIG. 2 is a graph depicting various pressure values that may be acquired from the NIBP monitoring system 10 depicted in FIG. 1. The cuff pressure as determined by the pressure transducer 26 is represented as cuff pressure graph 36. The cuff pressure peaks at 38*a* which is the cuff pressure at which the cuff 12 has been fully inflated as controlled by the processing unit 16. The processing unit 16 controls the inflation of the cuff 12 such that 38*a* is a pressure that is sufficiently above the systolic pressure of the patient. This may be controlled or modified by referencing previously determined values of patient blood pressure data by reference to standard medical practices, or blood pressure estimations. The cuff pressure graph 36 then incrementally lowers at a series of pressure steps 38*a*-38*u* which reflect each incremental pressure reduction in the cuff 12 as controlled by the deflate valve 24. Before the cuff pressure has reached a pressure step at which the patient brachial artery is no longer completely occluded, the measured cuff pressure will show oscillometric pulses 40. The number of oscillometric pulses detected at each pressure step is controlled as a function of the heart rate of the patient and the length of time that the NIBP system collects data at each pressure step, but typically cuff pressure data is recorded at each pressure level to obtain at least two oscillometric pulses.

The cuff pressure is measured at each of the pressure step increments, including the oscillometric pulse data until the cuff pressure reaches an increment such that the oscillometric pulses are small enough to completely specify the oscillometric envelope, such as found at pressure increment 38*u*. At this point, the processing unit 16 controls the deflate valve 24 to fully deflate the pressure cuff 12 and the collection of blood pressure data is complete.

FIG. 2 further depicts an oscillometric envelope 42 as calculated using the oscillometric pulse data collected from the series of incremental cuff pressure steps. The processing unit 16 isolates the oscillometric pulses at each pressure step, and creates a best fit curve to represent the oscillometric envelope 42. The oscillometric envelope is useful in estimating systolic pressure, diastolic pressure and MAP. The MAP 44 is determined as the pressure step increment 38*k* that corresponds to the peak 44 of the oscillometric envelope 42. Once the MAP has been determined, the systolic pressure 46 and diastolic pressure 48 may be identified as the pressure level values associated with particular oscillation amplitudes that are predetermined percentages of the oscillation amplitude at the MAP pressure level. In one embodiment, the systolic pressure 46 corresponds to pressure increment 38*h* where the oscillometric envelope amplitude is 50% that of the MAP. In another embodiment, the diastolic pressure 48 correlates to pressure increment 38*n* where the envelope amplitude is between 60% and 70% that of the envelope amplitude at MAP. The percentages of the MAP amplitude used to estimate the systolic pressure and the diastolic pressure are usually between 40% and 80% depending upon the specific algorithm used by the processing unit 16.

In an alternative embodiment, the amplitude of the oscillometric pulses at each pressure step are averaged to produce an oscillometric envelope data point. In some of these embodiments, techniques such as pulse matching or the elimination of the first and/or last oscillometric pulse at a pressure step may be used to improve the quality of the computed oscillometric data point. The oscillometric envelope 42 may also be created by using the average of the complex amplitudes at the pressure step as the input data points for a best-fit curve. Alternatively, data points of the oscillometric envelope 42 may be the maximum amplitude of the oscillometric pulses at each pressure step.

As can be seen, from FIG. 2, the oscillometric pulses are relatively small with respect to the overall cuff pressure and the pressure increment steps. This makes the detection of the oscillometric pulses highly susceptible to noise and other artifacts. While relatively high frequency noise, such as that above 20 Hz, can be filtered easily, the relatively small size of the oscillometric pulses makes it difficult to adequately filter artifacts due to human motion since these artifacts are typically at a lower signal frequency, such that the frequency of the artifact is similar to that of the oscillometric pulse signal.

The physiological monitoring system, and method of determining blood pressure as disclosed herein aim to provide improved processing of oscillometric pulse signals to remove artifacts of a similar frequency as the oscillometric pulses. Embodiments as disclosed herein may result in producing a higher quality oscillometric pulse signal when the desired physiological signal and the artifact have specific frequency content properties; this leads to increased accuracy in constructing the oscillometric envelope and computation of the patient blood pressure estimates. FIG. 2 demonstrates an example of acquisition of the oscillometric signals using step deflation; however, other techniques of obtaining the oscillometric signals, such as by continuous deflation, are possible, and the description given here is not meant to limit the usefulness of embodiments as disclosed below with respect to step deflation.

Figure 3:
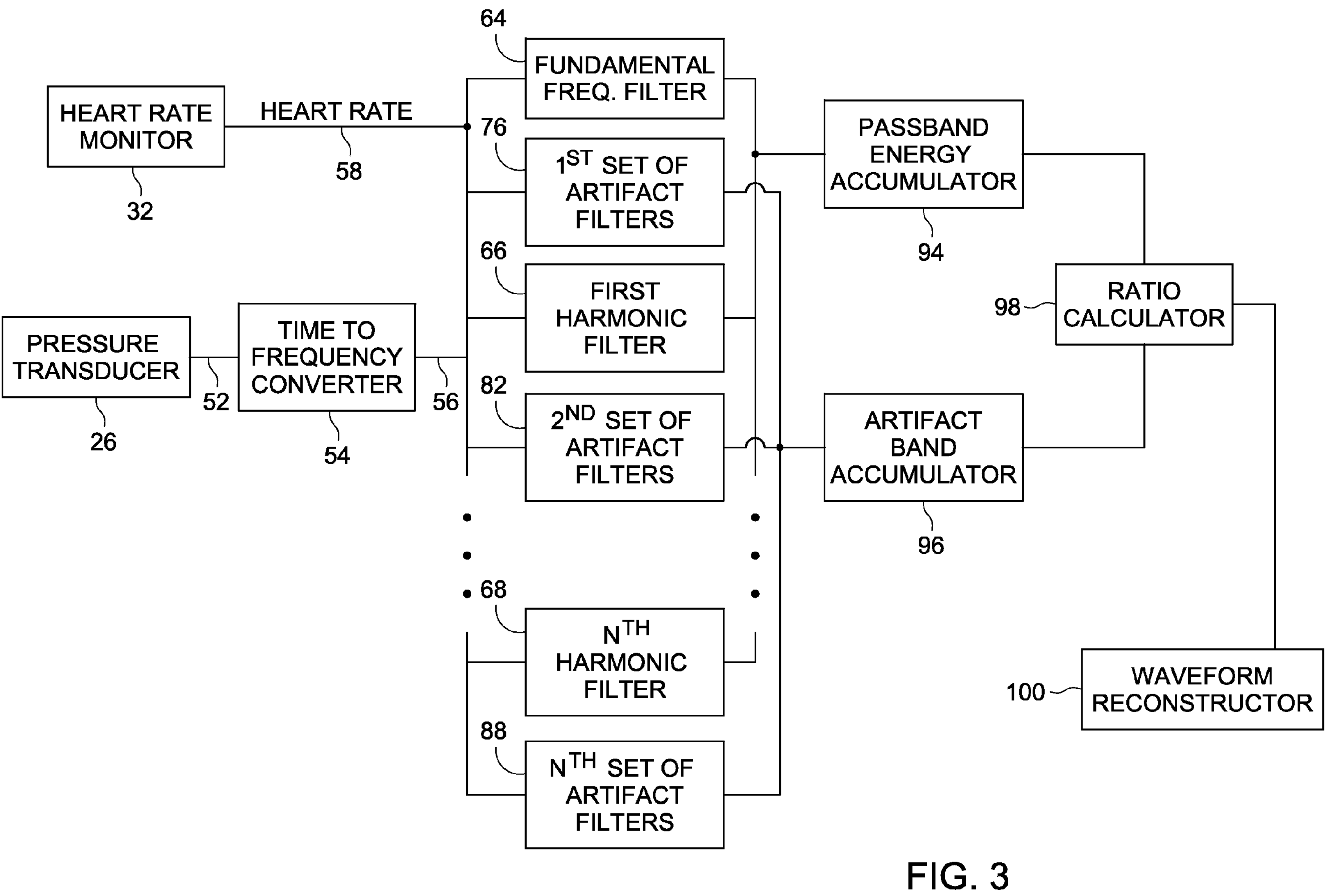
FIG. 3 is an embodiment of an oscillometric data processing system for the artifact resistant analysis of oscillometric data.

FIG. 3 depicts an embodiment of an oscillometric data processing system 50. The data processing system 50 includes the pressure transducer 26 that collects raw oscillometric pulse signals from the pressure cuff applied to the patient. The pressure transducer 26 may sample the cuff pressure at any suitable sampling rate. In one embodiment, the pressure transducer 26 may sample the cuff pressure at a rate of 400 samples per second; however, in other embodiments, 100 samples per second or any other sampling rate known to one skilled in the art may be utilized. In the embodiment illustrated, the cuff pressure is controlled so that each pressure increment step lasts approximately five seconds. However, the length of time of each pressure increment step may be modified in accordance with the present disclosure. In an exemplary embodiment for the purposes of discussion, the system may record five seconds of data at a sampling rate of 400 samples per second yielding an oscillometric pulse signal of approximately 2,000 samples for each pressure step. However, it is understood that a wide variety of sampling rates and/or pressure step lengths resulting in oscillometric pulse signals of a different number of samples may be utilized while operating within the scope of the present disclosure.

The raw oscillometric signal 52 is sent to a time-to-frequency converter 54. The time-to-frequency converter 54 may be a discrete Fourier transform algorithm (DFT). The time-to-frequency converter 54 converts the raw oscillometric signal from a time domain signal into a frequency domain signal. A more useful technique available for this conversion is the fast Fourier transform (FFT). The result of the time-to-frequency conversion is a signal that expresses the oscillometric signal with respect to its frequencies as opposed to expressing the signal with respect to time.

The data processing system 50 further includes the heart rate monitor 32 that acquires the heart rate of a patient at the time the raw oscillometric pulse signal is acquired. As previously stated, the heart rate monitor 32 may include ECG or $SpO_2$ techniques; however, in an alternate embodiment the heart rate may be determined using the frequency domain oscillometric signal obtained from the time-to-frequency converter 54.

Figure 4:
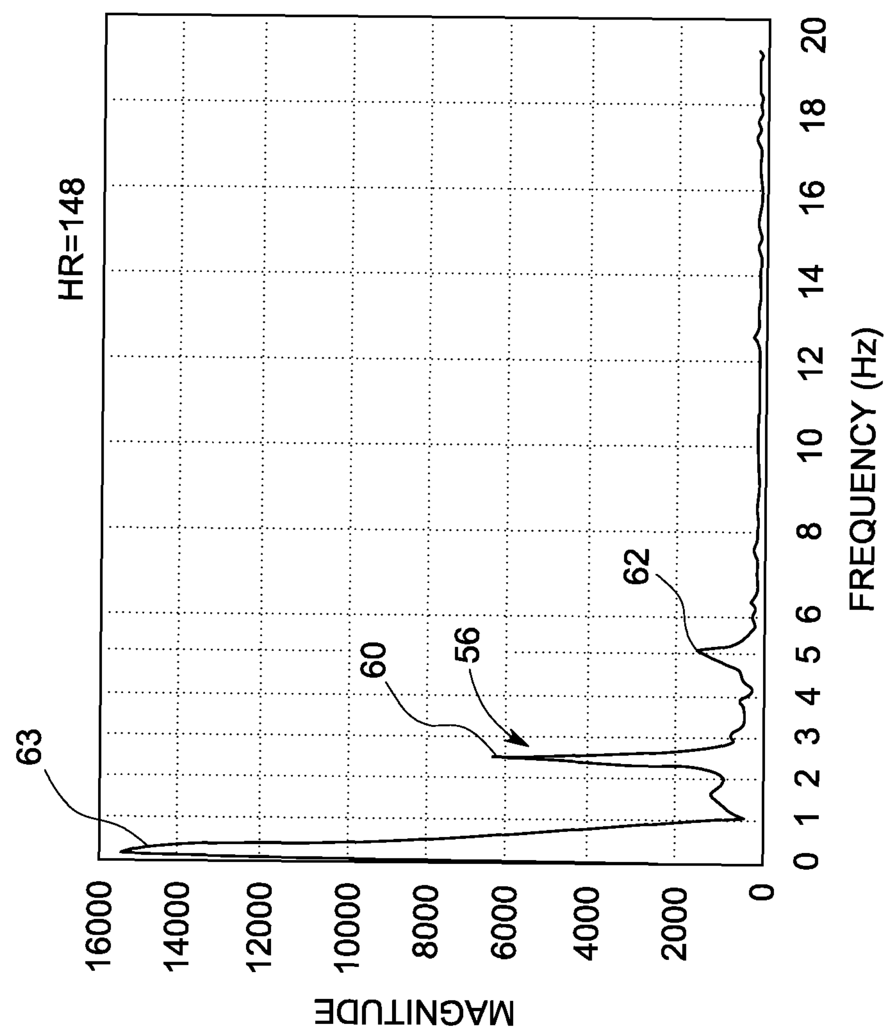
FIG. 4 is a graph of a frequency domain oscillometric signal from a patient.

Referring now to FIG. 4, thereshown is a first exemplary embodiment of the frequency domain oscillometric signal 56 that is generated by the time-to-frequency converter 54. In the embodiment of FIG. 4, the frequency domain signal 56 is from a patient having a heart rate of 148. As previously described, the heart rate from the patient is generated by the heart rate monitor 32 in FIG. 3 and is fed to various other components as will be described.

Referring back to FIG. 4, the frequency domain oscillometric signal 56 includes a first peak 60 that occurs at the fundamental frequency. In the embodiment shown in FIG. 4, the fundamental frequency is 2.46 Hz. A second peak 62 occurs near the first harmonic frequency of 4.93 Hz. Although not shown in FIG. 4, the frequency domain oscillometric signal 56 may have another peak at the second harmonic frequency of 7.40 Hz. A significant artifact 63 occurs below the fundamental frequency.

Figure 5:
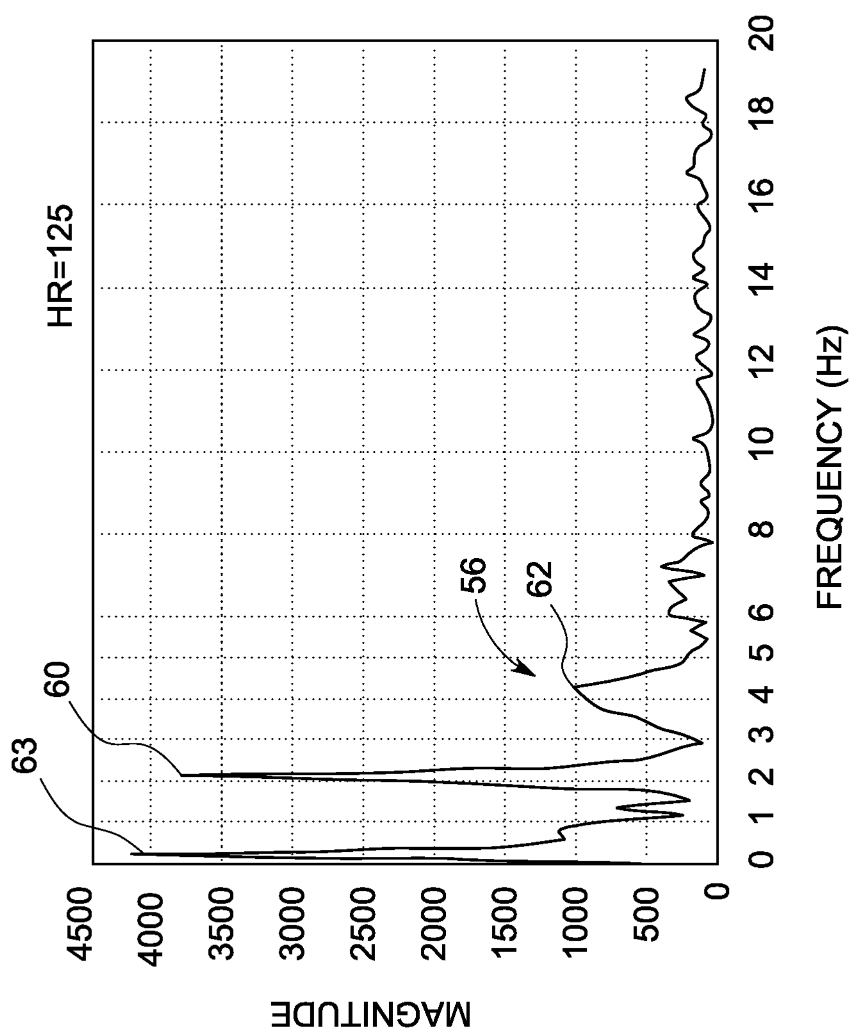
FIG. 5 is a second graph of a frequency domain oscillometric signal from a patient.

FIG. 5 illustrates yet another example of a frequency domain oscillometric signal 56. In the embodiment of FIG. 5, the heart rate of a patient is 125 such that the fundamental frequency is 2.08 Hz. As discussed previously, a first peak 60 occurs at the fundamental frequency and a second peak 62 occurs at the first harmonic frequency of 4.17 Hz. However, in the embodiment shown in FIG. 5, a significant amount of distortion occurs around the second peak 62 due to artifacts present in the oscillometric signal 56.

One known method of eliminating artifacts in the frequency domain oscillometric signal is to filter the signal using very narrow band pass filters that have pass bands centered around the fundamental frequency and one or more harmonic frequencies of the heart rate. An example of such a system is shown and described in U.S. Patent Application Publication No. 2009/0209868. Although such a system and method has proven effective in many cases, the system does not analyze the amount of energy in the frequency domain signal in areas other than the pass bands.

Referring back to FIG. 3, in accordance with the present disclosure, the heart rate 58 and the frequency domain oscillometric signal 56 is provided to a fundamental frequency filter 64, a first harmonic filter 56 and may be provided to any number of additional $n^{th}$ harmonic filters 68. Although not shown in FIG. 3, the fundamental frequency filter 64, the first harmonic filter 66 and the $n^{th}$ harmonic filter 68 are each associated with some type of processor or controller that receives the patient's heart rate 58 and computes the associated fundamental frequency and harmonic frequencies of the patient's heart rate 58. The frequency domain filters 64, 66 and 68 associated with each of the harmonic computers consists of a band pass filter of a reasonably narrow band width centered at the associated heart rate harmonic. The reasonably narrow band width for each of the pass bands may be 0.6 Hz; however, this is not intended to be limiting on the scope of the band width that may be utilized within the scope of the disclosure.

Figure 6:
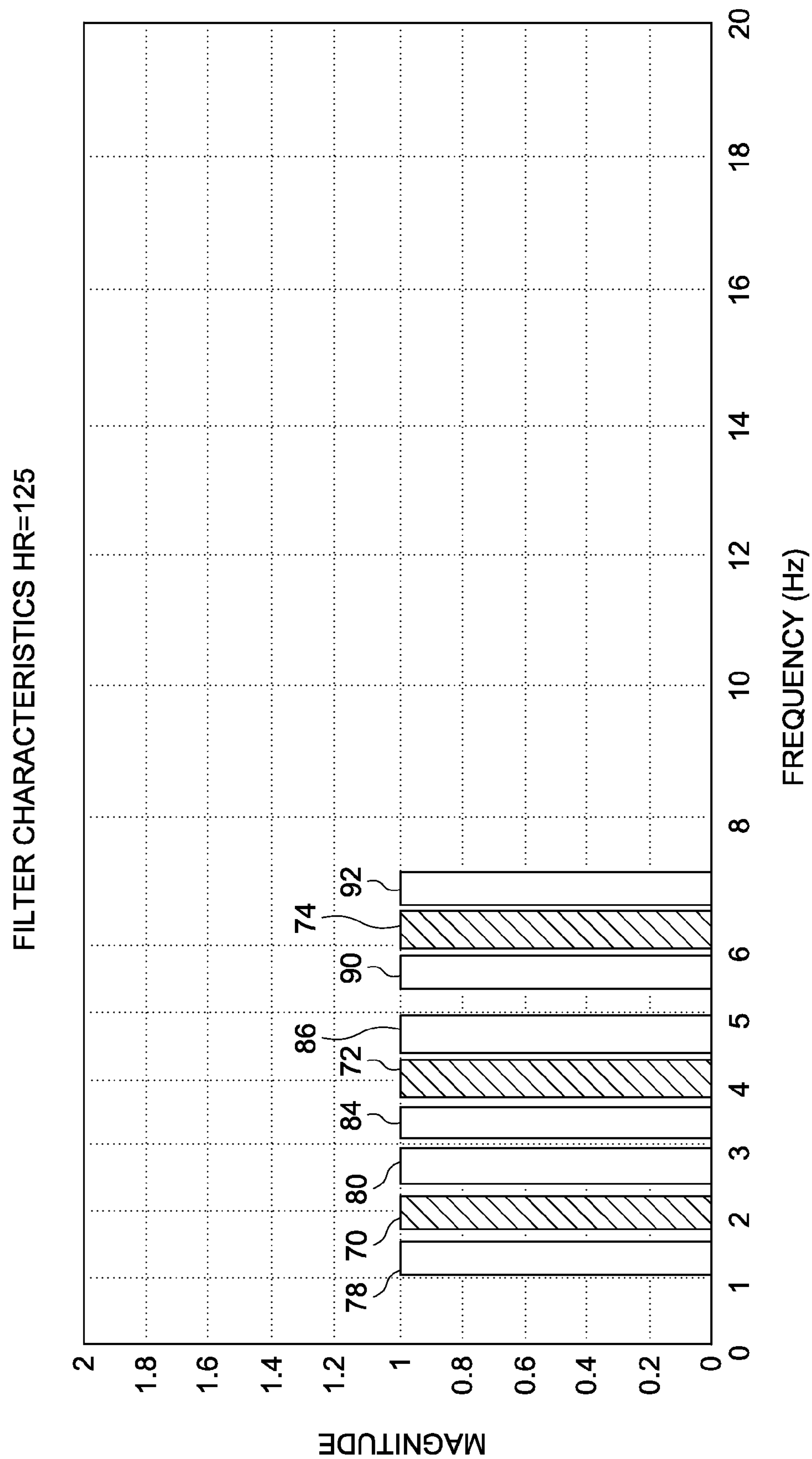
FIG. 6 is a graph depicting multiple pass bands and multiple artifact bands for the filtering system of the present disclosure.

Referring now to FIG. 6, in an embodiment utilized with a patient having a heart rate of 125, a fundamental frequency filter 64 creates a first pass band 70 centered around the fundamental frequency of 2.08 Hz. The first harmonic filter 66 creates a second pass band 72 centered around the first harmonic frequency of 4.17 Hz. In the embodiment of FIG. 6, a second harmonic filter creates the third pass band 74 centered around the second harmonic frequency of 6.25 Hz.

Referring back to FIG. 3, the oscillometric data processing system 50 includes multiple sets of artifact filters to isolate other portions of the frequency domain oscillometric signal. In the embodiment of FIG. 3, a first set of artifact filters 76 create an artifact band both above and below the fundamental frequency. In the embodiment shown in FIG. 6, the first set of artifact filters create a first artifact band 78 slightly below the first pass band 70 and a second artifact band 80 slightly above the first pass band 70. In the embodiment illustrated, each of the artifact bands 78, 80 has a band width that may be also in the range of 0.6 Hz, although other band widths are contemplated as being within the scope of the present disclosure.

Referring back to FIG. 6, a second set of artifact filters are utilized to create the third artifact band 84 slightly below the second pass band 72 and a fourth artifact band 86 slightly above the second pass band 72. The third and fourth artifact bands 84, 86 are again calculated by a computer processor associated with the first harmonic filter 66. In the embodiment of FIG. 6, the $n^{th}$ set of artifact filters create the fifth artifact band 90 and the sixth artifact band 92, as can be understood in FIGS. 3 and 6.

Once the frequency domain oscillometric signal 56 has passed through the fundamental frequency filter 64 and the harmonic filters 66 and 68, the energy within each of the pass bands are received in a pass band energy accumulator 94. The pass band energy accumulator 94 creates a summation of the energy within each of the pass bands described. Although the system shown in FIGS. 3 and 6 describes utilizing a fundamental frequency pass band and first and second harmonic pass bands, it should be understood that additional pass bands or fewer pass bands could be utilized while operating within the scope of the present disclosure.

As illustrated in FIG. 3, the amount of energy determined in the first set of artifact filters 76, the second set of artifact filters 82 and the $n^{th}$ set of artifact filters 88 are summed in an artifact band accumulator 96. Like the pass band energy accumulator 94, the artifact band accumulator 96 sums the detected energy in each of the artifact bands. In the embodiment shown in FIGS. 3 and 6, artifact bands are created on each side of the fundamental frequency and each of the harmonic frequencies. However, it should be understood that other types of artifact filters could be utilized while operating within the scope of the present disclosure.

Although the embodiment of FIGS. 3 and 6 utilizes artifact filters on each side of the fundamental frequency pass band and the harmonic frequency pass band, it should be understood that the system of FIG. 3 could instead accumulate all of the energy of the frequency domain oscillometric signal outside of the pass band. In such an embodiment, separate filters would not be required for the artifact bands and instead the energy of the frequency domain oscillometric signal in portions of the signal outside of the pass bands would be accumulated by the artifact band accumulator 96.

A ratio calculator 98 is utilized to create a ratio of the energy within the pass bands, as determined by the pass band energy accumulator, to the energy in the artifact bands, as determined by the artifact band accumulator 96. The ratio calculator 98 can be utilized to implement Equation 1 set forth below.

$$R_{artifact} = \frac{\sum_{artfact} |F_i|^2}{\sum_{physio} |F_i|^2} \qquad \text{Equation 1}$$

As the equation set forth above indicates, the ratio is the energy within the artifact bands over the energy in the pass bands. Alternatively, the equation could be inverted such that the ratio would be the energy within the pass bands over the energy within the artifact bands. Further, the energy within the artifact bands could be the energy of the frequency domain oscillometric signal outside of the pass bands, as previously described. As will be described in greater detail below, based upon the calculated ratio, the system and method of the disclosure can modify the operation of the oscillometric data processing system 50.

Once the ratio calculator 98 has calculated the ratio set forth above by Equation 1, the system 50 can then calculate the envelope data point for the current pressure of the blood pressure cuff. A waveform reconstructor 100 shown in FIG. 3 operates to reconstruct the oscillometric signal based upon the portions of the frequency domain oscillometric signal within each of the pass bands centered around the fundamental frequency and the selected harmonic frequency. Examples of methods of operating the system of the present disclosure will now be described.

Figure 7:
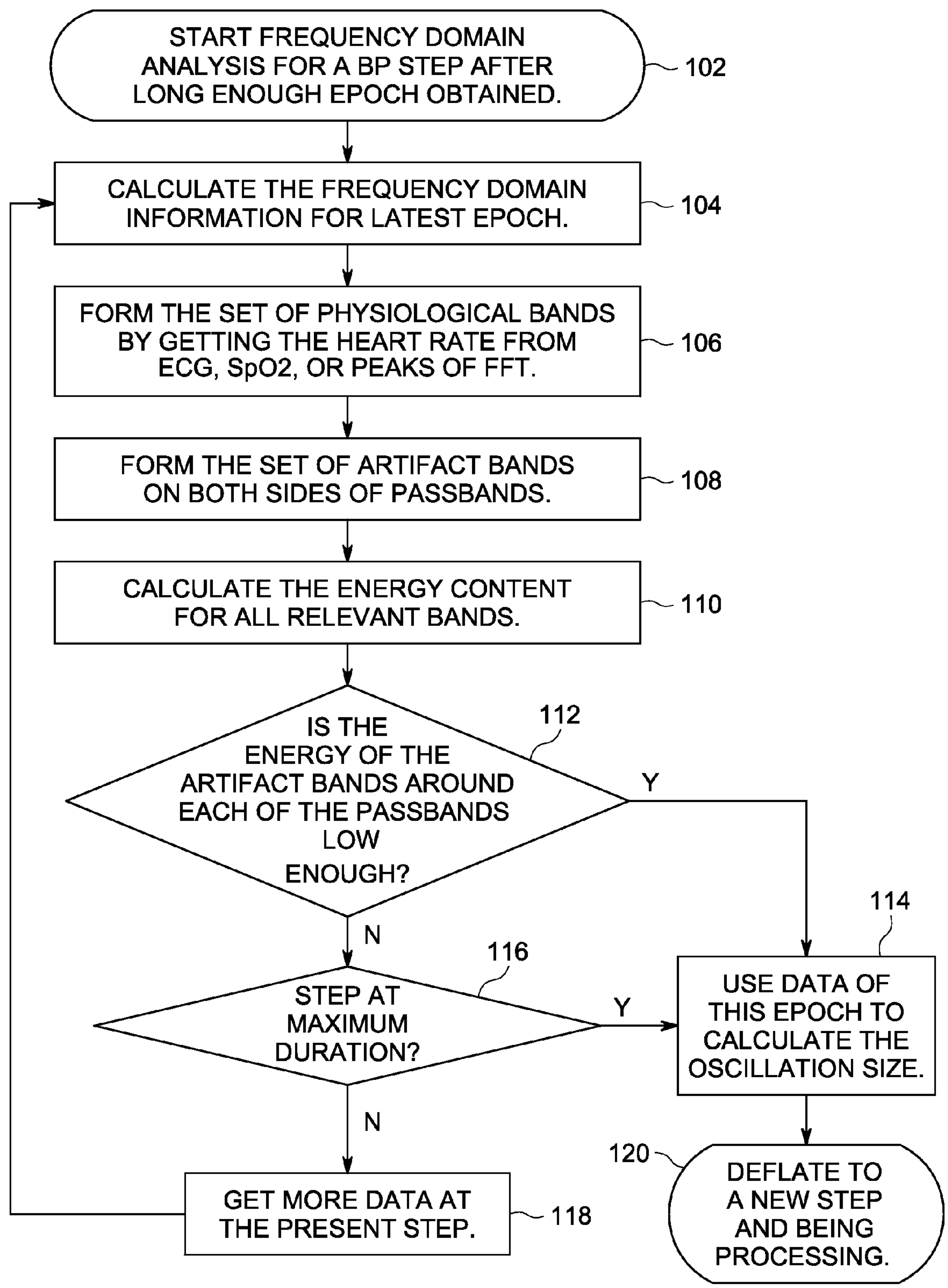
FIG. 7 is a flowchart illustrating the operational sequence of the system of the present disclosure.

Referring now to FIG. 7, the first method of operating the oscillometric data processing system 50 of the present disclosure is shown and described. Initially, the system receives an oscillometric signal from the pressure transducer pneumatically connected to the blood pressure cuff at a current pressure step, as illustrated in step 102. As previously described, the system may acquire the oscillometric data from the blood pressure cuff at a selected sampling rate for a predetermined period of time, such as approximately five seconds.

Once the oscillometric data signal has been acquired, the system utilizes the time-to-frequency converter 54 of FIG. 3 to calculate the frequency domain information for the most recent epoch, as illustrated by step 104. FIG. 4 illustrates one example of the frequency domain oscillometric signal for a patient having a heart rate of 148 bpm.

In addition to receiving the oscillometric data signal from the patient, the system also receives the heart rate from the heart rate monitor. Based upon the heart rate received from the heart rate monitor, the system adaptively forms the set of pass bands, as shown in step 106. As previously described, the pass bands are defined around the fundamental frequency and one or more of the harmonic frequencies, each of which are determined based upon the patient heart rate. In FIG. 3, the pass bands are defined by the fundamental frequency filter 64, the first harmonic filter 66 and the $n^{th}$ harmonic filter 68.

In one embodiment of the disclosure, the system then adaptively creates a set of artifact bands on each side of the pass bands, as illustrated in step 108. FIG. 6 illustrates the first and second artifact bands 78, 80 on either side of the first pass band 70.

Once the pass bands and artifact bands have been defined, the system calculates the energy content for each of the relevant pass bands and artifact bands, as illustrated in step 110. In step 110, the system can calculate the energy within each individual band or can accumulate the energy within all of the pass bands and all of the artifact bands.

In the method of FIG. 7, the system determines whether the energy of each of the artifact bands on each side of the pass band is sufficiently low such that the frequency domain oscillometric signal is acceptable for further processing, as illustrated in step 112. As an example, the system calculates the energy within the first and second artifact bands 78, 80 shown in FIG. 6 and compares the energy relative to the energy within the first pass band 70. If the combined energy within the first and second artifact bands 78, 80 is sufficiently low, the system uses the data within the first pass band 70 to calculate the oscillometric data point, as illustrated in step 114. During this processing step, the system also compares the energy within the third and fourth artifact bands 84, 86 relative to the energy within the second pass band 72. If the energy within the third and fourth artifact bands 84, 86 is sufficiently low, the energy within the second pass band is also utilized to calculate the oscillometric data point in step 114.

During step 112, the system can perform many different types of calculations. As an example, the system can compare the combined energy within the first, second and third pass bands 70, 72 and 74 to the energy either within the combination of all of the artifact bands or other portions of the frequency domain oscillometric signal outside of the pass bands. Typically, the energy in the pass bands is compared to the energy outside of the pass bands and, if the ratio described by Equation 1 is below a threshold, the system proceeds to step 114. However, if the comparison made in step 112 does not meet the predetermined threshold or the ratio of Equation 1, the system moves to step 116 and determines whether the blood pressure cuff has remained at the current pressure level for more than a maximum duration. As an example, the maximum duration that the blood pressure cuff can remain at any pressure step may be 20 seconds. If the blood pressure cuff has not been on the current step for the maximum duration, the system proceeds to step 118 to gather additional oscillometric data at the current pressure step. Once this additional data is gathered in step 118, the system returns to step 104 and again calculates the various pass bands and artifact bands, as previously described.

If the system determines at step 116 that the maximum duration for the pressure step has been reached, the system moves to step 114 and utilizes the data at the pressure step in the calculation of the oscillation size. Although the data may not be optimal, the system determines that the pressure within the cuff has remained at a current level for the maximum duration and the system moves to step 114.

After step 114, the system deflates the blood pressure cuff in step 120 and returns to step 102 for the new pressure step.

As can be understood in the method illustrated by FIG. 7, the system performs a comparison of the energy within one or more pass bands to the energy either within artifact bands or other portions of the frequency domain oscillometric signal to determine whether the energy within the pass bands is sufficient to provide a good signal for processing. The system operated in accordance with FIG. 7 does not reduce the pressure within the blood pressure cuff to the next pressure step until an acceptable signal has been received or the step duration limit has occurred. In this manner, the system only reduces the pressure within the blood pressure cuff when the energy within the pass band is sufficiently high relative to the artifacts outside of the pass band so as to provide an adequate signal or when a long enough period of time has occurred that the best strategy is to move to the next cuff pressure level.

Figure 8:
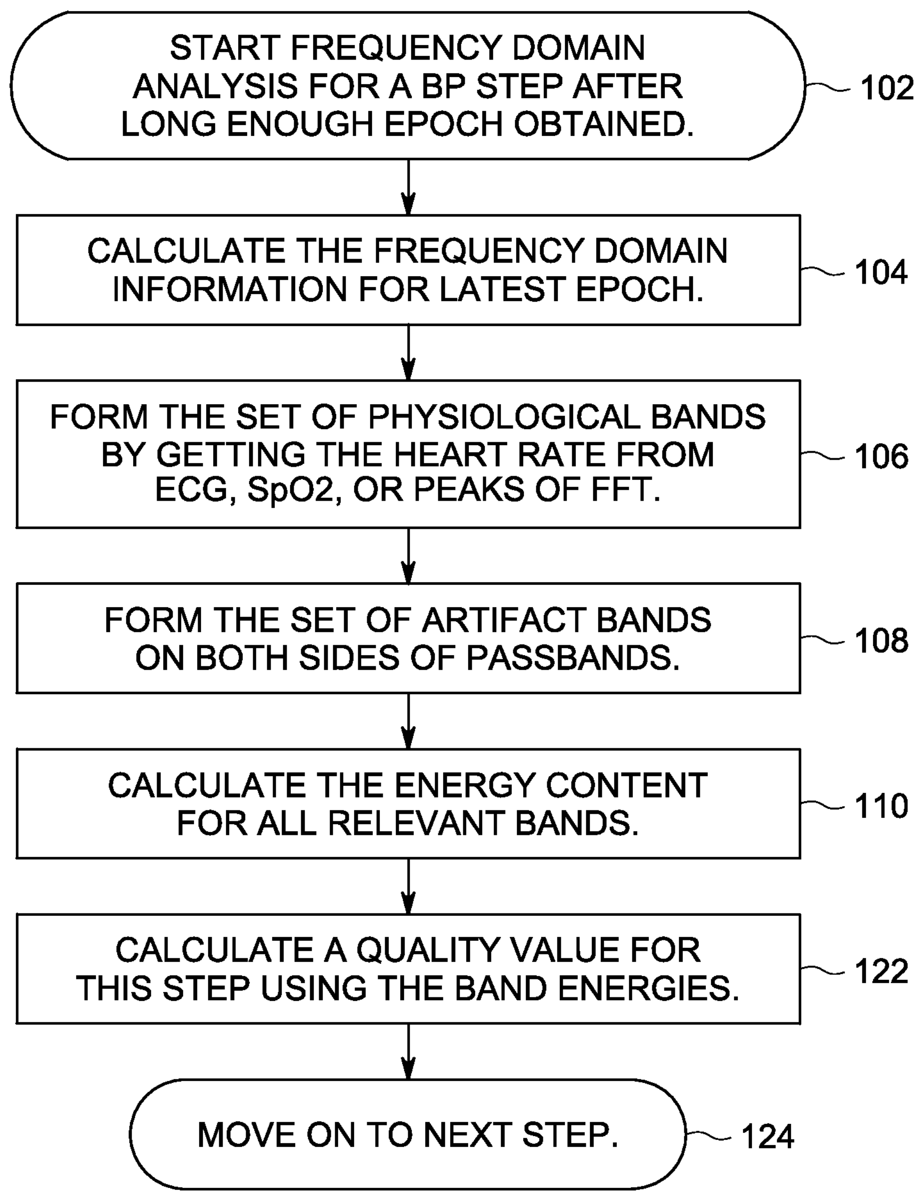
FIG. 8 is a flowchart illustrating a second embodiment of the operational sequence of the system of the present disclosure.

Referring now to FIG. 8, thereshown is yet another method of operating the oscillometric data processing system of the present disclosure. The method shown in FIG. 8 begins with the same processing steps 102-110 as described in FIG. 7. However, after the energy content has been calculated in step 110 for all of the relevant pass bands and artifact bands, the system determines in step 122 a quality value for the current pressure step utilizing the calculated band energies. The quality value is a relative value that relates the energy within the selected pass bands to the energy outside of the pass bands, such as within the multiple artifact bands previously described. If the energy within the pass bands is significantly higher than the energy outside of the pass bands, the signal will calculate a quality value that can be displayed along with the blood pressure measurement. It is contemplated that the quality value could be presented as either a numeric value or a color or graphic indication showing the relative quality of the signal obtained from the blood pressure cuff. In this manner the quality information from each cuff pressure step can be combined so that the display of the calculated blood pressure can be quantified as to whether the signal is of high quality, medium quality or low quality. Additionally, such a frequency domain measure of the quality could be used to decide whether or not to publish blood pressure estimates or not.

Although FIG. 8 is shown as calculating the quality value before moving to the next pressure step in step 124, it should be understood that step 122 could also be incorporated into the method shown in FIG. 7. As an example, the quality value could be calculated between steps 114 and 120 in FIG. 7 while operating within the scope of the present disclosure.

As described above, the oscillometric data processing system 50 shown and described in FIG. 3 and the other drawing Figures can be utilized to perform multiple functions to quantify and determine the energy within pass bands relative to other portions of a frequency domain oscillometric signal. In one embodiment, the energy within one or more pass bands that are each based upon the fundamental frequency of the patient are compared to the energy outside of the pass bands such that the system can determine how long the blood pressure cuff should remain at a distinct pressure step before moving to the next pressure step. Further, the system can be utilized to determine which of the pass bands should be utilized to calculate the envelope data point for the current pressure step. As described, the system compares the energy within each pass band to energy immediately adjacent to the pass bands to determine whether the energy within the pass band is of high quality. Next, the system and method of the present disclosure can be utilized to provide an indication of the quality of the blood pressure determination by comparing the energy within one or more of the pass bands to the energy outside of the pass bands. Other uses of the system and method of the present disclosure are contemplated as being within the scope of the present disclosure.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

We claim:

1. A method of computing an oscillometric envelope for use in determining the blood pressure of a patient, the method comprising the steps of:

receiving an oscillometric signal from a blood pressure cuff positioned on the patient;

receiving an indication of the heart rate of the patient;

computing a fundamental frequency of the heart rate;

converting the oscillometric signal to the frequency domain;

filtering the frequency domain oscillometric signal using a band pass filter having a first pass band centered around the fundamental frequency;

calculating the energy of the frequency domain oscillometric signal in a first noise band having a defined first frequency range having an upper limit and a lower limit below the first pass band;

calculating the energy of the frequency domain oscillometric signal in a second noise band having a defined second frequency range having an upper limit and a lower limit above the first pass band;

combining the calculated energy in the first and second noise bands to define the energy within the defined noise bands;

calculating the energy of the frequency domain oscillometric signal in the first pass band centered around the fundamental frequency;

calculating a ratio of the energy of the frequency domain oscillometric signal within the defined noise bands to the energy of the frequency domain oscillometric signal within the first pass band;

reconstructing the oscillometric signal from the filtered frequency domain signal in the first pass band only when the calculated ratio is below a threshold; and computing an oscillometric envelope data point from the reconstructed oscillometric signal only when the calculated ratio is below the threshold.

2. The method of claim 1 wherein the step of converting the oscillometric signal to the frequency domain is performed using a fast Fourier transform (FFT).

3. The method of claim 1 further comprising the steps of:

computing at least a first harmonic frequency of the heart rate;

filtering the frequency domain oscillometric signal using a second band pass filter having a second pass band centered around the first harmonic frequency;

calculating the energy of the frequency domain oscillometric signal in the second pass band;

combining the calculated energy within the second pass band with the calculated energy within the first pass band; and calculating the ratio based upon the combined energy.

4. The method of claim 1 further comprising the steps of:

computing at least a first harmonic frequency of the heart rate;

filtering the frequency domain oscillometric signal using a second band pass filter having a. second pass band centered around the first harmonic frequency;

calculating the energy of the frequency domain oscillometric signal in the second pass band centered around the first harmonic frequency;

calculating the energy of the frequency domain oscillometric signal in a third noise band having a defined third frequency range having an upper limit and a lower limit below the second pass band and a fourth noise band having a defined fourth frequency range having an upper limit and a lower limit above the second pass band;

calculating a second ratio of the energy in the second pass band to the energy in the combination of the third and fourth noise bands; and reconstructing the oscillometric signal from the filter frequency domain signal using only the first or second pass band if the first or second pass bands have a ratio below the threshold.

5. The method of claim 1 wherein the received oscillometric signal is from a single pressure step for the blood pressure cuff and the computed data point is at the single pressure step, further comprising the step of repeating the method at a plurality of blood pressure cuff pressure steps to compute a plurality of envelope data points.

6. The method of claim 5 further comprising the steps of:

obtaining additional oscillometric signals at each of the pressure steps when the calculated ratio exceeds the threshold; and reducing the pressure of the blood pressure cuff to the next pressure step when the calculated ratio is below the threshold.

7. A method of processing oscillometric data for use in determining the blood pressure of a patient, the method comprising:

receiving an oscillometric signal from a blood pressure cuff connected to the patient;

receiving an indication of the heart rate of the patient;

computing a fundamental frequency and at least one harmonic frequency of the heart rate;

converting the oscillometric signal to the frequency domain;

filtering the frequency domain signal with a first pass band centered at the fundamental frequency and a second pass and centered at the at least one harmonic frequency;

determining the energy of the frequency domain oscillometric signal in the combination of the first and second pass bands;

calculating the energy of the frequency domain oscillometric signal in a first noise band having a defined first frequency range having an upper limit and a lower limit below the first pass band and in a second noise band having a defined second frequency range having an upper limit and a lower limit above the first pass band;

calculating the energy of the frequency domain oscillometric signal in a third noise band having a defined third frequency range having an upper limit and a lower limit below the second pass band and in a fourth noise band having a defined fourth frequency range having an upper limit and a lower limit above the second pass band;

combining the calculated energy in the first, second, third and fourth noise bands to define the energy within the defined noise bands;

calculating a ratio of the energy of the frequency domain oscillometric signal within the defined noise bands to the energy of the frequency domain oscillometric signal within the first and second pass bands;

reconstructing the oscillation signal from the filtered frequency domain signal in the pass bands when the calculated ratio is below a threshold; and computing an oscillometric envelope data point for the current pressure within the blood pressure cuff based upon the reconstructed oscillometric signal.

8. The method of claim 7 wherein the step of converting the oscillometric signal to the frequency domain is performed using a fast Fourier transform (FFT).

9. The method of claim 7 wherein the oscillometric signal is received at a pressure step, further comprising the steps of:

obtaining additional oscillometric signals at the pressure step when the calculated ratio exceeds the threshold; and reducing the pressure of the blood pressure cuff to a subsequent pressure step when the calculated ratio is below the threshold.

10. The method of claim 7 wherein the frequency domain oscillometric signal is filtered at least at a first harmonic frequency and a second harmonic frequency.

11. The method of claim 7 further comprising the steps of comparing the energy in the noise bands above and below each of the pass bands to the energy within each of the pass bands; and disregarding the energy in each pass band when the energy in the noise bands exceeds a threshold relative to the energy in the pass band.

12. The method of claim 7 further comprising the step of presenting a quality indicator that is based on the energy in the pass band relative to the energy outside of the pass band.

13. The method of claim 12 wherein the quality indicator is a visual indicator.

* * * * *